US009227079B2

(12) United States Patent
Sunagawa et al.

(10) Patent No.: US 9,227,079 B2
(45) Date of Patent: Jan. 5, 2016

(54) STIMULATION DEVICE AND METHOD FOR TREATING CARDIOVASCULAR DISEASE

(71) Applicant: KYUSHU UNIVERSITY, NATIONAL UNIVERSITY CORPORATION, Fukuoka (JP)

(72) Inventors: Kenji Sunagawa, Fukuoka (JP); Tomomi Ide, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 14/197,356

(22) Filed: Mar. 5, 2014

(65) Prior Publication Data
US 2015/0025298 A1 Jan. 22, 2015

Related U.S. Application Data

(63) Continuation-in-part of application No. 13/257,583, filed as application No. PCT/JP2010/002016 on Mar. 19, 2010, now abandoned.

(60) Provisional application No. 61/161,456, filed on Mar. 19, 2009.

(51) Int. Cl.
*A61N 1/00* (2006.01)
*A61N 2/02* (2006.01)
*A61N 1/36* (2006.01)
*A61N 2/00* (2006.01)

(52) U.S. Cl.
CPC .............. *A61N 2/02* (2013.01); *A61N 1/36053* (2013.01); *A61N 1/36114* (2013.01); *A61N 2/006* (2013.01); *A61N 1/36117* (2013.01); *A61N 1/36153* (2013.01); *A61N 1/36171* (2013.01); *A61N 1/36175* (2013.01); *A61N 2/002* (2013.01)

(58) Field of Classification Search
USPC ....................................... 607/9, 119
See application file for complete search history.

(56) References Cited

U.S. PATENT DOCUMENTS

| 5,991,665 | A | * | 11/1999 | Wang et al. ..................... 607/61 |
| 2003/0212440 | A1 | * | 11/2003 | Boveja ............................ 607/46 |
| 2006/0100668 | A1 | * | 5/2006 | Ben-David et al. ............... 607/2 |
| 2007/0038259 | A1 | * | 2/2007 | Kieval et al. .................... 607/44 |

(Continued)

FOREIGN PATENT DOCUMENTS

| JP | 2005-500863 A | 1/2005 |
| JP | 2008-296014 A | 12/2008 |

(Continued)

OTHER PUBLICATIONS

Magstim Air-Cooled Double 70mm Coil System: Operating Manual 1600-23-04, The Magstim Company Limited U.K., 1999.

(Continued)

*Primary Examiner* — Nicole F Lavert
(74) *Attorney, Agent, or Firm* — Konomi Takeshita

(57) ABSTRACT

A stimulation device and method for treating cardiovascular disease in a human or an animal is provided, the method including placing a magnetic pulse application unit including a coil on a skin surface of a region of the human or the animal, and generating magnetic pulses around the coil, wherein the magnetic pulses induce currents in tissues in the region to stimulate a vagus nerve. The region may be a neck region or a chest region.

21 Claims, 11 Drawing Sheets

(56) References Cited

U.S. PATENT DOCUMENTS

| | | | |
|---|---|---|---|
| 2008/0004672 A1* | 1/2008 | Dalal et al. | 607/44 |
| 2008/0091255 A1 | 4/2008 | Caparso et al. | |
| 2008/0300642 A1 | 12/2008 | Inagaki et al. | |

FOREIGN PATENT DOCUMENTS

| | | |
|---|---|---|
| JP | 2009-233024 A | 10/2009 |
| WO | 02/45791 A2 | 6/2002 |
| WO | 2008/045434 A2 | 4/2008 |

OTHER PUBLICATIONS

Chris Hovey BSc and Reza Jalinous PhD, The Guide to Magnetic Stimulation, The Magstim Company Limited U.K. Jul. 21, 2006.

Reza Jalinous, A Guide to Magnetic Stimulation, The Magstim Company Limited, U.K. Mar. 1, 1998.

Vol. 4 Magnetic Stimulation Technical Note for Research, http://www.miyuki-net.co.jp/jp/seminar/msTechnicalNote/msTechnicalNote.shtml, MG Miyuki Giken, May 2012.

Takaki Tsutsumi et al, Modulation of the myocardial redox state by vagal nerve stimulation after experimental myocardial infraction. Cardiovascular Research Mar. 2008,1;77, 713-721.

Takaki Tsutsumi et al, Effect of anaesthesia-induced alterations in haemodynamics on in vivo kinetics of nitroxyl probes in electron spin resonance spectroscopy. Free Radical Research, Apr. 2008; 42(4): 305-311.

\* cited by examiner

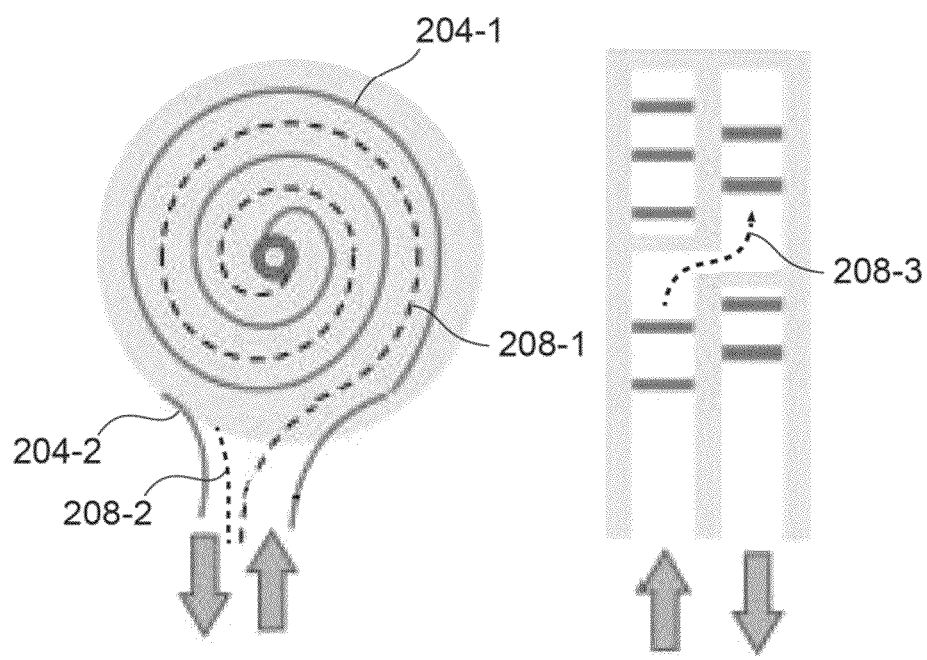
FIG. 11A
FIG. 11B
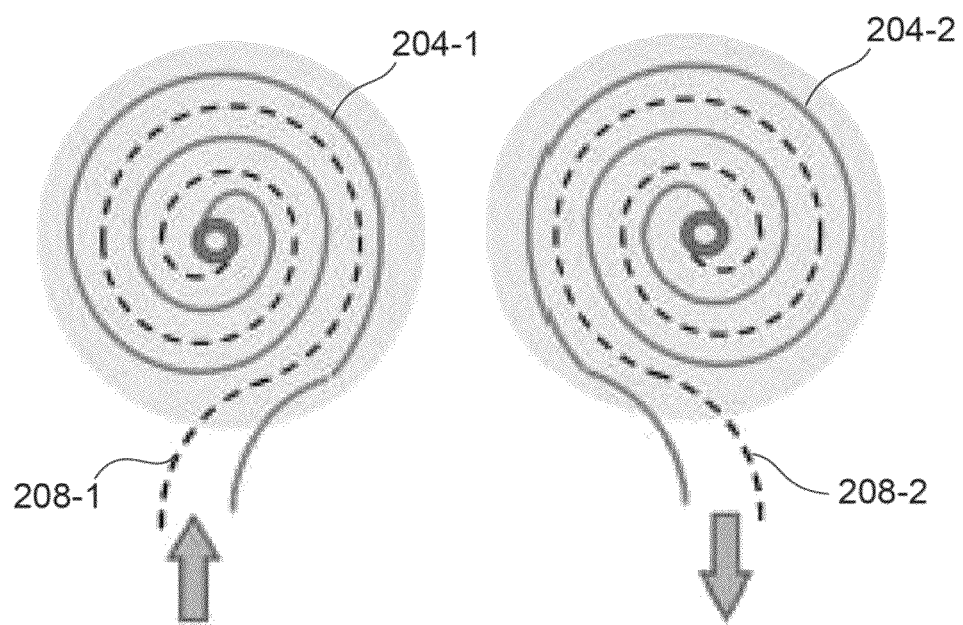
FIG. 11C
FIG. 11D

STIMULATION DEVICE AND METHOD FOR TREATING CARDIOVASCULAR DISEASE

CROSS REFERENCE TO RELATED APPLICATIONS

This application is a continuation-in-part of U.S. patent application Ser. No. 13/257,583, filed on Feb. 3, 2012, which is a national phase application of PCT application No. PCT/JP2010/002016, filed on Mar. 19, 2010, which claims priority from U.S. provisional application Ser. No. 61/161,456, filed on Mar. 19, 2009.

FIELD OF THE INVENTION

The present invention relates to electrical and magnetic stimulation devices and methods for treating humans and animals with cardiovascular disease.

More specifically, the stimulation device for treating cardiovascular disease of the present invention applies stimulation to the vagus nerve in the neck region of a human or an animal. The stimulation can be generated electrically or magnetically.

BACKGROUND

Myocardial infarction is a kind of ischemic heart disease, and is a state in which the amount of blood flow in coronary artery as nutrition to the heart drops, the heart muscle becomes ischemic and the heart dies. Normally, this refers to an acutely occurring "acute myocardial infarction (AMI)". The method of treatment during the acute phase is as a rule complete rest. During the acute phase after the onset of disease, it is easy for lethal arrhythmia to occur, and the danger of dying is extremely high. The more the ischemic period is prolonged, the more death of the heart muscle advances, and an irreversible decrease of cardiac performance occurs. When disease is first suspected, it is necessary to immediately call an ambulance while keeping an eye on the patient, and in the case that the patient become unconscious and there is no pulse, it becomes necessary to perform heart massage without hesitation. When functional cardiac arrest occurs, going three to five minutes or more without performing treatment results in a rehabilitation rate of nearly zero. It is necessary to start emergency treatment (heart massage or the like) without waiting for the ambulance to arrive.

Myocardial infarction is caused by insufficient relative and absolute oxygen supply to the heart muscle; and as a method of treatment, the patient is kept quiet in bed and oxygen inhalation is performed. In some cases morphine may also be administered in order to relieve pain and reduce oxygen consumption. The main objective during the acute phase is to prevent lesion expansion of myocardial infarction. Generally, the treatment performed as first aid for myocardial infarction is centered on "oral administration of aspirin", "oxygen inhalation", "administration of morphine" and "administration of nitrate", and is known by the name "MONA", taking the first letter from Morphine, Oxygen, Nitrate and Aspirin.

By actively performing reperfusion therapy of the obstructed coronary artery within six hours or less from the onset of the myocardial infarction, it is possible to reduce the range of necrosis of the heart muscle. Not being limited to this, in an example of a case within 24 hours from the onset of the illness, performing reperfusion therapy is highly meaningful. Generally, treatment may be divided into the case of performing catheter therapy (PTCA, PCI), or thrombolytic therapy (PTCR), and different treatment policies are adapted depending on the country, insurance or doctor's judgment. In Japan, many facilities are capable of performing PCI, and in many cases, PCI is performed during the acute phase. However, because examination and treatment are performed via an artery, complications often occur. Particularly, when a rise in ST is seen on the electrocardiogram, it is essential that PCI be performed as soon as possible, however, there are a few hospitals, even in the USA, which is a leading nation in the treatment of heart disease, that take the position of performing the same treatment immediately after the patient has been admitted to emergency. In the case of there being three or more sites of stenosis, there are some facilities that will perform emergency coronary artery bypass graft surgery (CABG). In comparing PCI and CABG, for PCI restenosis occurs in 25 to 30% of cases, so even in the case of single-vessel disease, there are cases where CABG has advantages. However, since 2004, drug-eluting stents (DES) are covered by insurance, so an improvement in the result of PCI treatment is expected. When intervention is successful during the acute phase, relative prognosis is often maintained. Intervention is one method for treating illness of the heart, blood vessels, the liver, the brain, digestive organs, urinary organs and the like, and is mainly a treatment method for performing treatment by inserting a small tube called a catheter into a blood vessel from a small hole having a diameter of several mm that is made in the skin. Intervention is a method of treatment that has very little burden on the patient, and recently has attracted much attention. The cut is small, so recovery after surgery is fast, and after a very short hospital stay of three to five days, together with greatly improving the QOL (Quality of Life) of the patient, this treatment reduces the financial burden on the patient, and is said to even contribute to health care cost-containment measures by the government. However, in reperfusion therapy such as intervention, complications such as arrhythmia, extrasystole, ventricular fibrillation, atrioventricular block or heart failure often occur.

Quick cardiovascular recovery is essential for maintaining life, however, exposes oneself to danger. Reperfusion increases localized damage, and produces an inflammatory reaction that also leads to systemic insult. Acute onset of myocardial infarction, stroke, cardiac arrest and the like can produce ischemia-reperfusion injury (IRI). However, many scheduled surgical treatments such as organ transplants and aneurysm treatment require a period of ischemia between treatments, and therefore may produce the onset of IRI. Conventionally it was thought that the existence of inflammatory cells in the ischemic tissue indicated a pathophysiological response to injury. However, according to laboratory tests, it has been shown that inflow to inflammatory cells, and particularly to macrophage tissue, which is a phagocyte, even though important for recovery, also brings about tissue damage that exceeds the tissue damage caused by ischemia alone. This damage can have an effect on various kinds of tissue such as the heart, brain, liver, spleen, intestines, lungs and pancreas.

Various methods for putting an end to reperfusion injury such as induced hypothermia, controlled reperfusion, ischemic preconditioning and the like have been reported. Induced hypothermia is the introduction of moderately low temperature (28° C. to 32° C.) to a patient. Mild induced hypothermia is thought to suppress many chemical reactions related to reperfusion injury. Regardless of these potential benefits, induced hypothermia also brings about side effects such as arrhythmia, infection, blood clotting and the like. Controlled reperfusion means to control the initial stage of reperfusion by performing reperfusion of tissue at low pressure using blood that has been altered so that there is hyperosmosis, alkalosis, and substrate concentration. Ischemic preconditioning is intentionally causing short-term ischemia, which has a protective effect, to occur by slowing down cellular metabolism between the onset of more prolonged ischemia. These treatments are useful in a surgical setting (for example, before or after scheduled heart surgery), however, normally, these treatments are not suitable in a preset condition that is controlled as required.

In recent years, applying electrical stimulation to the vagus nerve has been reported as an effective treatment method for chronic heart failure. In other words, when electrical stimulation of the vagus nerve is performed, the heart rate drops, and as the heart rate drops, the myocardial oxygen consumption is reduced, and a state of oxygen deprivation in the heart muscle is prevented or improved. As a result, the occurrence of myocardial ischemia and the accompanying lethal arrhythmia are prevented, so this method is considered to be effective as treatment for or prevention of heart failure. Technology has been disclosed related to a vagus nerve stimulation system for performing electrical stimulation of the vagus nerve, and particularly, technology has been disclosed related to a vagus nerve stimulation system that is capable of indirectly stimulating the vagus nerve from under the skin or from the surface of the skin (Japanese Patent Application laid-open publication No. 2005-500863, Japanese Patent Application laid-open publication No. 2009-233024).

BRIEF DESCRIPTION OF THE DRAWINGS

FIGS. 11A-11D illustrate an air flow pattern along the coil winding, which is configured to be double-layered in this example.

DETAILED DESCRIPTION

Figure 1:
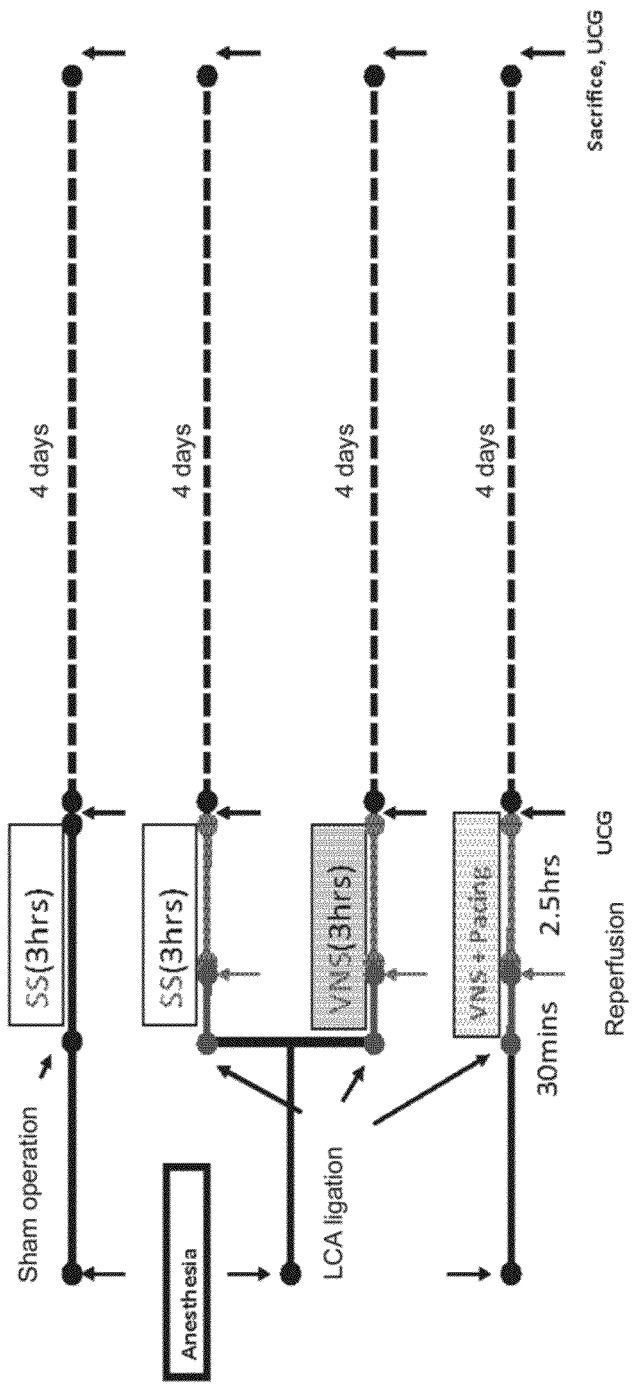
FIG. 1 illustrates the test protocol of an embodiment of the present invention.

Considering the above situation, the purpose of the present invention is to provide a new treatment method and device that are capable of improving a drop in myocardial contractility, suppressing the occurrence of arrhythmia, and reducing the size of infarction when treating cardiovascular disease such as acute myocardial infarction. The present inventors took notice of the effect of treating cardiovascular disease by applying electrical or magnetic stimulation to vagus nerves. The case of applying electrical stimulation is explained first in the following.

Specifically, the present invention provides a treatment method and device for treating cardiovascular disease by applying electrical stimulation to the vagus nerve in the neck region of a human or an animal under specified conditions. By applying electrical stimulation to the neck region under certain conditions in this way, a superior treatment effect that prevents the occurrence of the above mentioned complications during treatment of cardiovascular disease becomes possible. By using the present invention to perform treatment by vagus nerve stimulation during emergency transport, it is possible to significantly lower the occurrence of complications after ischaemia reperfusion.

According to a first major aspect of the present invention, an electrical stimulation device for treating cardiovascular disease is provided that comprises at least one electrode that is placed on a nerve site inside an animal, and an electrical stimulation application unit that applies electrical stimulation to the vagus nerve in the neck region of the animal by the electrode.

According to an embodiment of the present invention the electrical stimulation device for treating cardiovascular disease can be applied to treatment of acute myocardial infarction. The electrical stimulation device for treating cardiovascular disease of the present invention displays an excellent effect in the treatment of cardiovascular disease, particularly in the treatment of acute myocardial infarction.

Moreover, according to another embodiment of the present invention, the conditions for applying electrical stimulation when treating cardiovascular disease with the electrical stimulation can be a voltage of 0.1 to 5 V, a frequency of 1 to 30 Hz and a pulse width of 500 μsec. By applying electrical stimulation to the vagus nerve in the neck region under these conditions, it is possible to prevent complications that accompany treatment, and to obtain excellent therapeutic effect.

Furthermore, with another embodiment of the invention, the amount of time that electrical stimulation is applied using the electrical stimulation application unit can be at least 0.5 hour and no greater than 10 hours. By applying electrical stimulation for an amount of time within this range, effective treatment of cardiovascular disease is possible.

According to a second major aspect of the present invention, a method for treating cardiovascular disease in a human or an animal is provided that comprises steps of: placing an electrode in contact with the vagus nerve in the neck region of the human or the animal; and applying an electrical stimulation by the electrode.

According to another embodiment of the present invention, the method for treating cardiovascular disease of this invention can be applied when the cardiovascular disease is acute myocardial infarction. The method for treating cardiovascular disease of the present invention particularly displays an effect when the cardiovascular disease is acute myocardial infarction.

Moreover, according to another embodiment of the present invention, it is possible for the step of applying an electrical stimulation of this method for treating cardiovascular disease to be used in combination with reperfusion therapy. By using the treatment method of this invention in combination with reperfusion therapy, even more effective treatment of cardiovascular disease can be expected. The step of applying an electrical stimulation of the present invention can be performed after the occurrence of acute myocardial infarction and before performing reperfusion therapy.

Furthermore, according to another embodiment of the present invention the conditions of a voltage of 0.1 to 5 V, a frequency of 1 to 30 Hz, and a pulse width of 500 μsec or greater can be applied as the conditions for applying electrical stimulation in the method for treating cardiovascular disease of this invention. By applying electrical stimulation under these conditions, it is particularly possible to perform effective treatment with no adverse effects such as complications.

Any kind of device can be used as the electrical stimulation device for treating cardiovascular disease of the present invention as long as it is a device having at least one electrode that can be placed at the site of a nerve, and has an electrical stimulation unit for applying electrical stimulation to the vagus nerve of a human or an animal by way of the electrode. The electrical stimulation unit can comprise, for example, a DC voltage generating circuit that generates a specified voltage, a capacitor that is charged by voltage that is generated by the DC voltage generating circuit, and a switch that is located between the capacitor and the electrode and that is for switching ON/OFF a connection between the capacitor and electrode.

In the electrical stimulation device for treating cardiovascular disease of the present invention, the electrode applies electrical stimulation by coming in direct contact with the vagus nerve of an animal. Here, the vagus nerve refers mainly to a parasympathetic nerve that controls the internal organs of the thoracicoabdominal region, and also involved in adjustment of the heart rate, peristaltic movement of the stomach and intestines, perspiration, and speech. This vagus nerve runs from the brain stem to the abdominal region.

Figure 7:
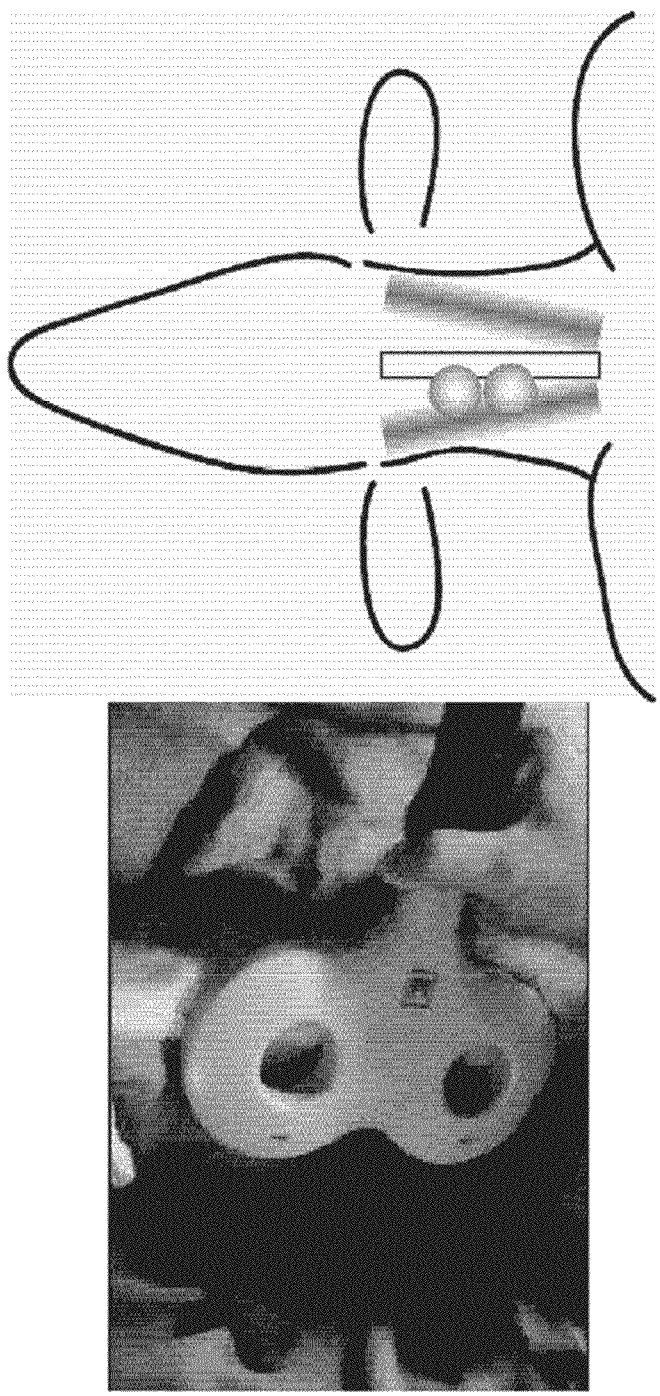
FIG. 7 is a drawing illustrating the site of electrical stimulation in an embodiment of the present invention.

In the present invention, the site of stimulation by the electrode is not particularly limited as long as it on a site of the vagus nerve, however, preferably the electrical stimulation is applied to the vagus nerve in the neck region. FIG. 7 illustrates the electrical stimulation site in the neck region in an embodiment of the present invention. When electrical stimulation is applied to a site of the vagus nerve by the electrode, the site of the vagus nerve to which the electrical stimulation is applied can be peeled back and exposed, for example, and the electrical stimulation can be applied by bringing the electrode in direct contact with the site. It is also possible to apply acupuncture stimulation to an acupuncture point that stimulates the vagus nerve, or apply electrical stimulation from inside a blood vessel.

The electrical stimulation device for treating cardiovascular disease of the present invention can be constructed with only an electrode and electrical stimulation application unit as described above, so from the aspect of compactness and convenience of operation, treatment by stimulation of the vagus nerve can even be performed during emergency transport. By being able to perform treatment by stimulation of the vagus nerve during emergency transport, it becomes possible to effectively lower the occurrence of complications after ischemia reperfusion.

The electrical stimulation device for treating cardiovascular disease of the present invention can be applied to various kinds of cardiovascular disease that are particularly treatable by stimulating the vagus nerve. For example, the device can be applied to treatment such as acute myocardial infarction, angina including unstable angina, heart failure, arrhythmia, hypertension, arteriosclerosis, and the like, and is particularly effective in the treatment of acute myocardial infarction and heart failure.

Conditions for applying electrical stimulation using the electrical stimulation device for treating cardiovascular disease of the present invention can be suitably set according to conditions that meet the severity of the patient's condition, and can be set within the range: a voltage of 0.01 to 20 V, frequency of 0.1 to 40 Hz, and pulse width of 500 μsec or greater. For example, in an embodiment of the present invention, conditions of a voltage of 0.1 to 5 V, frequency of 1 to 30 Hz, and pulse width of 500 μsec or greater are applied.

The time that electrical stimulus is applied in the present invention can be appropriately selected to correspond to the severity of the patient, however should be selected between 0.1 to 10 hours, or more preferably between 0.5 to 10 hours. The electrical stimulus can be applied intermittently at fixed time intervals, or can be applied continuously for a fixed time. After electrical stimulation has been applied for a fixed time, electrical stimulation can be applied again in the case that disease such as arrhythmia occurs.

Moreover, the method for treating cardiovascular disease of the present invention can be performed in combination with reperfusion therapy. When performed in combination with reperfusion therapy, the application of electrical stimulation can be performed before reperfusion therapy, can be performed at the same time as reperfusion therapy or can be performed after reperfusion therapy, however, preferably the electrical stimulation of the present invention is performed before performing the reperfusion therapy.

Figure 9:
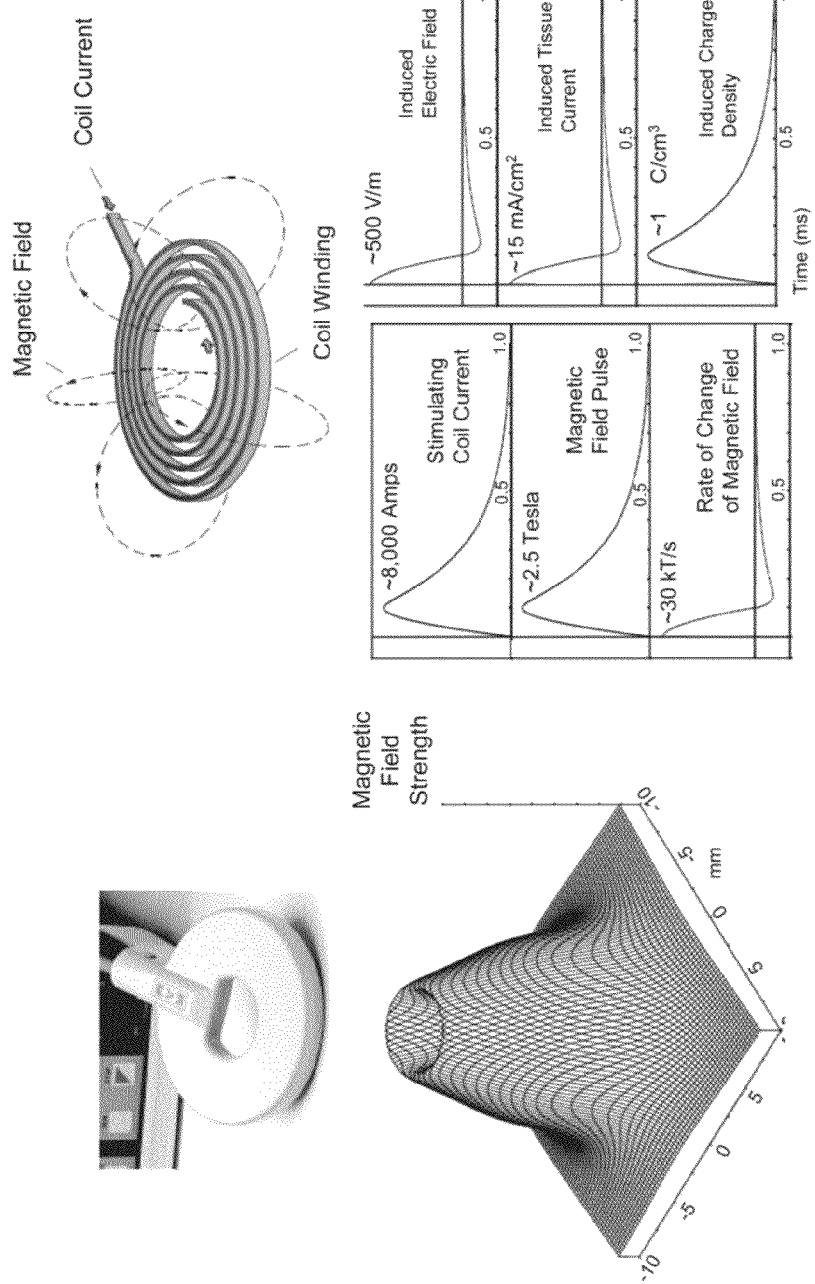
FIG. 9 is a drawing illustrating an example of a magnetic pulse application unit that can be used in the present invention.

Application of electrical stimulation is performed as the method for treating cardiovascular disease in the present invention, however, in addition to this, magnetic stimulation can also be used. For example, transcranial magnetic stimulation is performed using a magnetic stimulator that uses a coil for treating depression, however, by using a magnetic stimulation device to apply magnetic stimulation to the neck area of an animal, the same effects of lowering the heart rate and stimulating the vagus nerve can be obtained (FIG. 9).

Next, the effect of the present invention will be explained by illustrating an embodiment. However, the present invention is not limited to the embodiment described below, and it is understood that various changes and modification can be easily performed by one skilled in the art.

Embodiment 1

Thoracotomy was performed under anesthesia for a male SD rat, the left coronary artery was ligated, and after 30 minutes of ischemia, reperfusion was performed by loosening the ligature, which created myocardial infarction (MI). The right neck region was peeled to expose the vagus nerve, and stimulation of the vagus nerve was performed under the conditions of a 0 to 3V voltage, 1 msec pulse width and 5 Hz frequency so that a heart rate that was lowered by about 10% was obtained. Vagus nerve stimulation (VS) was performed for at least 30 minutes from the time of ischemia. After 24 hours, evaluations of the infarct area and apoptosis were performed, and after 4 days, evaluation of the hemodynamics was performed.

Figure 2:
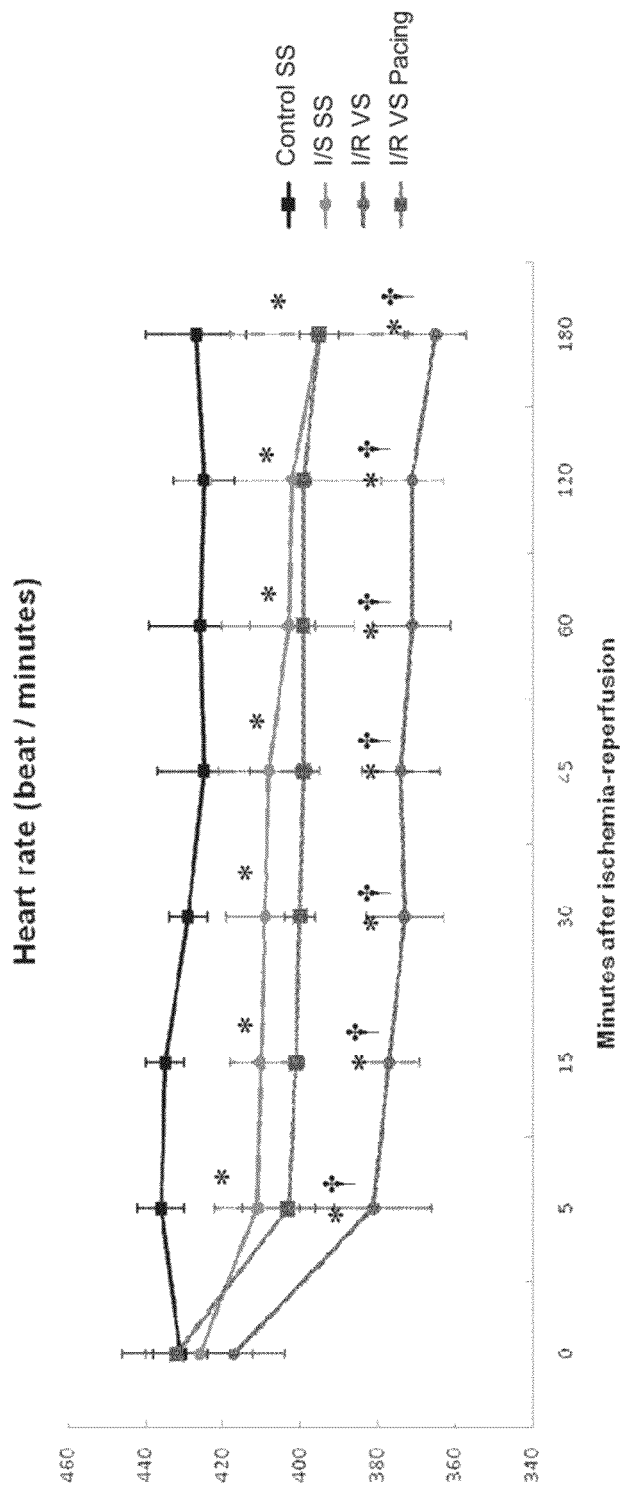
FIG. 2 is a graph illustrating the change in heart rate during stimulation of the vagus nerve in an embodiment of the present invention.

As a control, a group was made in which only a thoracotomy was performed, and as sham stimulation (SS), only an electrode was mounted without applying current. Moreover, in order to study the effect of bradycardia that occurs as the heart rate drops due to stimulation of the vagus nerve, pacing (VNS+pacing) was performed electrically in the right atrium during stimulation of the vagus nerve so that the heart rate could be maintained the same as in the SS group. The experimental protocol described above is illustrated in FIG. 1, and the change in the heart rate during stimulation of the vagus nerve is illustrated in FIG. 2.

Figure 3:
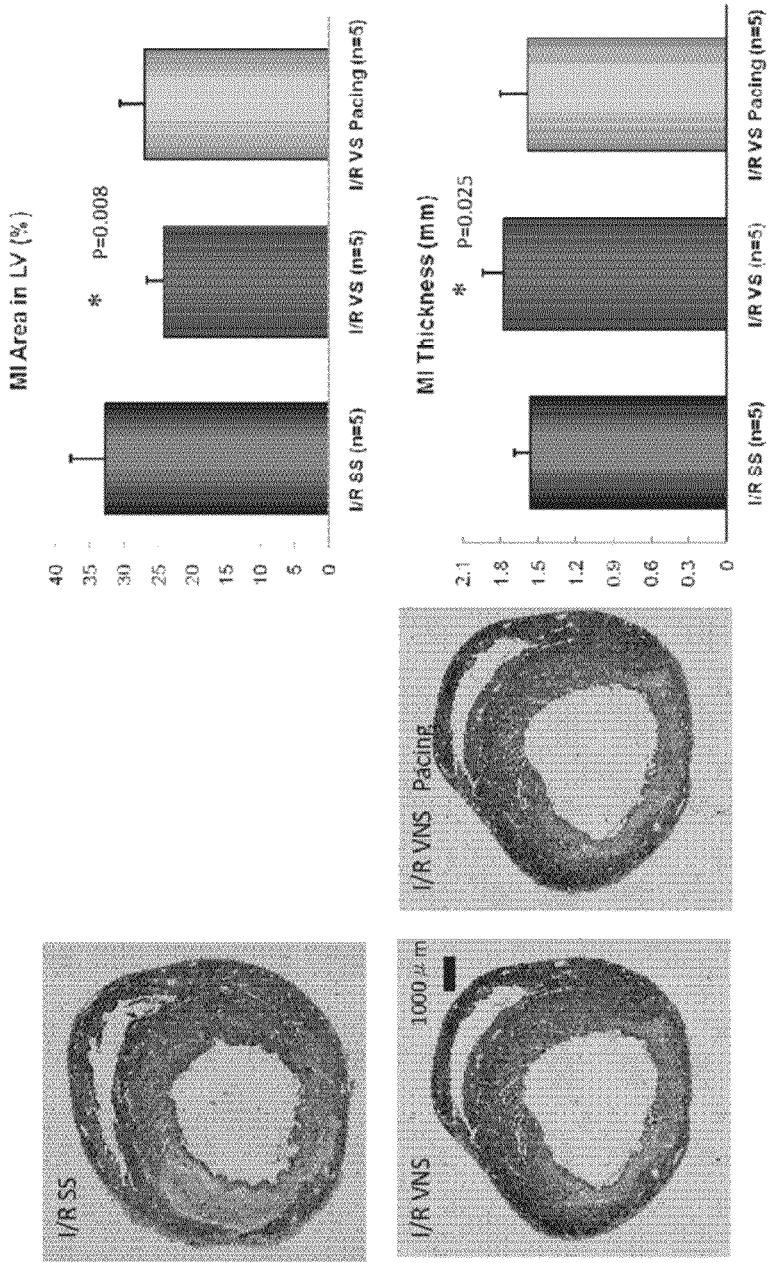
FIG. 3 is a drawing illustrating the infarction area that is suppressed by stimulation of the vagus nerve in an embodiment of the present invention.

It became clear from analysis after four days that during stimulation of the vagus nerve, the infarct area was significantly reduced. That result was partially reversed by pacing (FIG. 3). The results of measuring the hemodynamics four days later are illustrated in Table 1.

TABLE 1

| Change in Hemodynamics 4 Days After Ischaemia Reperfusion | | | | |
|---|---|---|---|---|
| Heart rate (bbp) | 417 ± 17 | 415 ± 7 | 417 ± 12 | 424 ± 11 |
| Left ventricular end-diastolic dimension (mm) | 5.4 ± 0.3 | 7.5 ± 0.5 * | 6.6 ± 0.5 *† | 6.6 ± 0.7 * |
| Left ventricular end-systolic dimension (mm) | 2.6 ± 0.2 | 5.9 ± 0.6 * | 4.4 ± 0.6 *† | 5.1 ± 0.6 * |
| Ejection fraction (%) | 51.5 ± 3.2 | 21.6 ± 4.2 * | 31.7 ± 6.2 *† | 23.9 ± 2.6 * |
| Infarct wall thickness (mm) | 1.9 ± 0.2 | 1.3 ± 0.2 * | 1.4 ± 0.2 * | 1.3 ± 0.2 * |
| Non-infarct wall thickness (mm) | 2.3 ± 0.3 | 1.9 ± 0.2 * | 2.0 ± 0.2 | 1.9 ± 0.1 * |
| Catheter Measurement Value (Under Anesthesia) | | | | |
| Heart rate (bpm) | 419 ± 8 | 409 ± 7 | 410 ± 14 | 424 ± 11 |
| Blood pressure (mmHg) | 119 ± 4 | 100 ± 5 | 102 ± 8 * | 106 ± 7 * |
| Left ventricular diastolic end pressure (mmHg) | 4.1 ± 1.6 | 7.2 ± 4.0 * | 3.8 ± 2.1 | 4.6 ± 1.0 |
| Maximum left ventricular dp/dt (mmHg/s) | 13700 ± 1700 | 8300 ± 300 * | 9900 ± 1800 *† | 8300 ± 1000 * |
| Minimum left ventricular dp/dt (mmHg/s) | −9700 ± 1600 | −6400 ± 700 * | −7500 ± 1300 * | −6400 ± 400 * |

Figure 4:
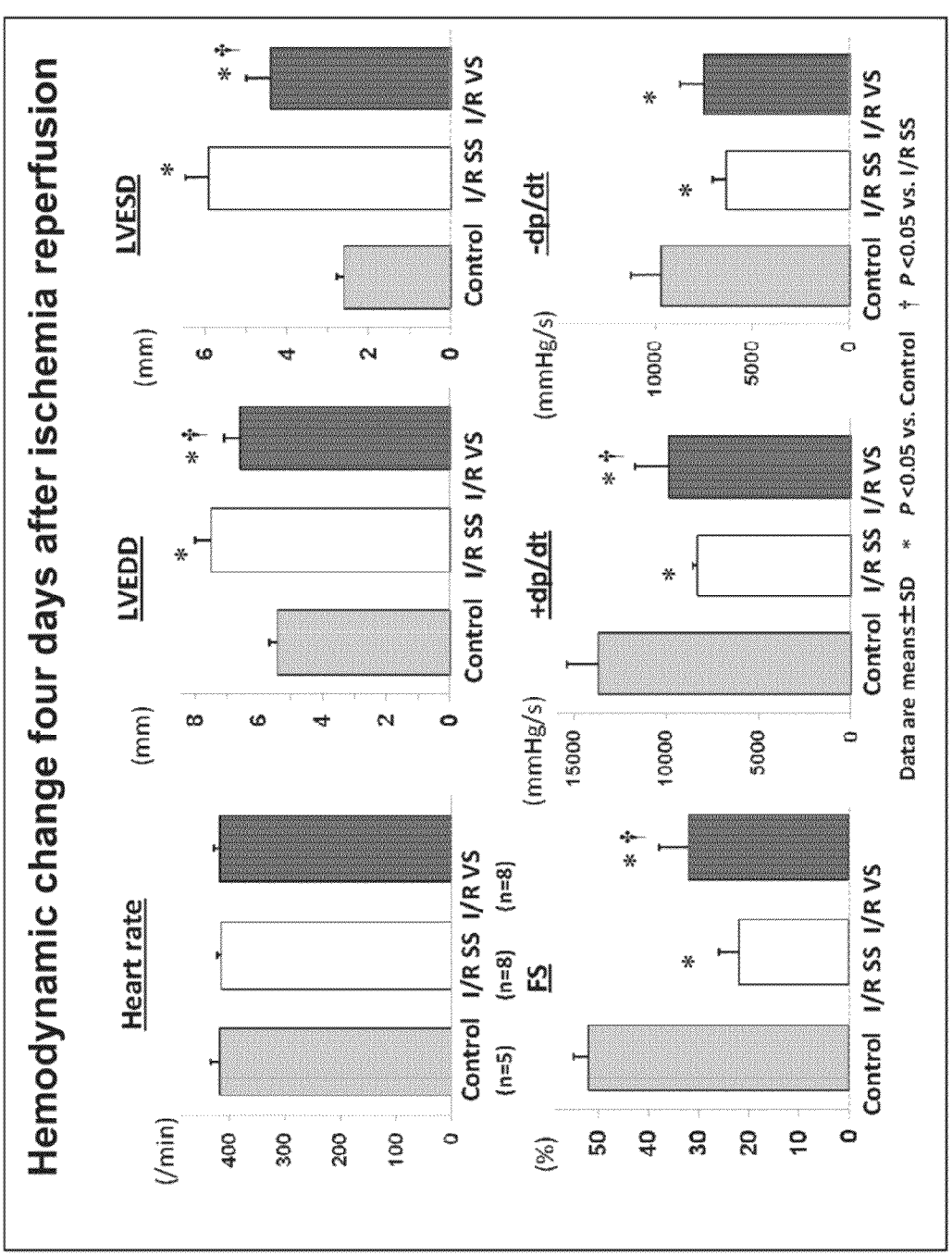
FIG. 4 is a table illustrating the hemodynamic change four days after ischemia reperfusion.

Data Notation: Average ± standard deviation
* $P < 0.05$ vs. Control SS (sham stimulation);
† $P < 0.05$ vs. I/R SS A graph of the results in Table 1 is illustrated in FIG. 4. A change in heart rate was seen, however, it is thought that stimulation of the vagus nerve significantly suppressed an increase in the left ventricle and a drop in the ejection rate that occur after ischaemia reperfusion, and suppressed myocardial remodeling.

Figure 5:
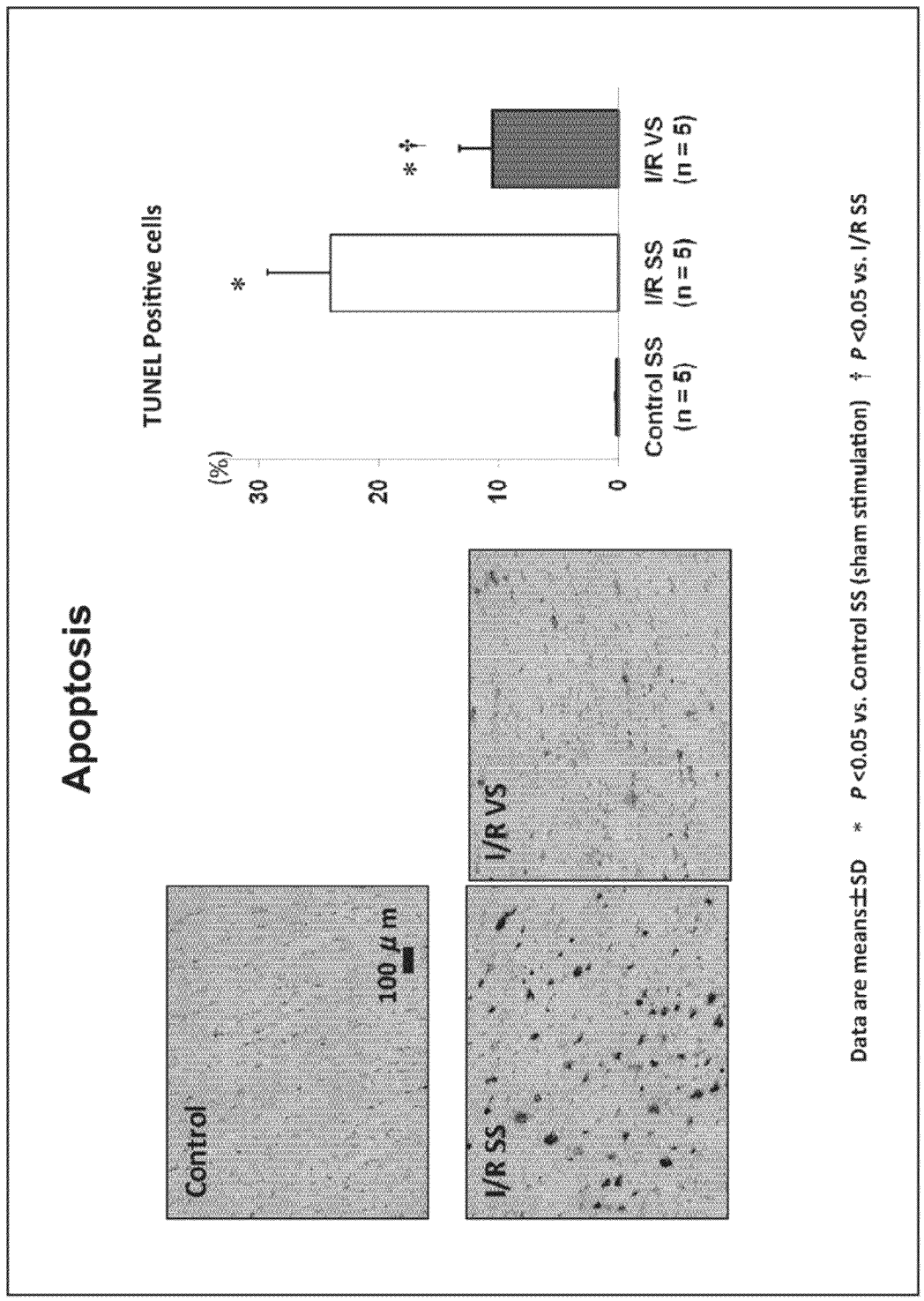
FIG. 5 is a drawing illustrating the ratio of TUNEL staining in the infarction area 24 hours after ischemia.
Figure 6:
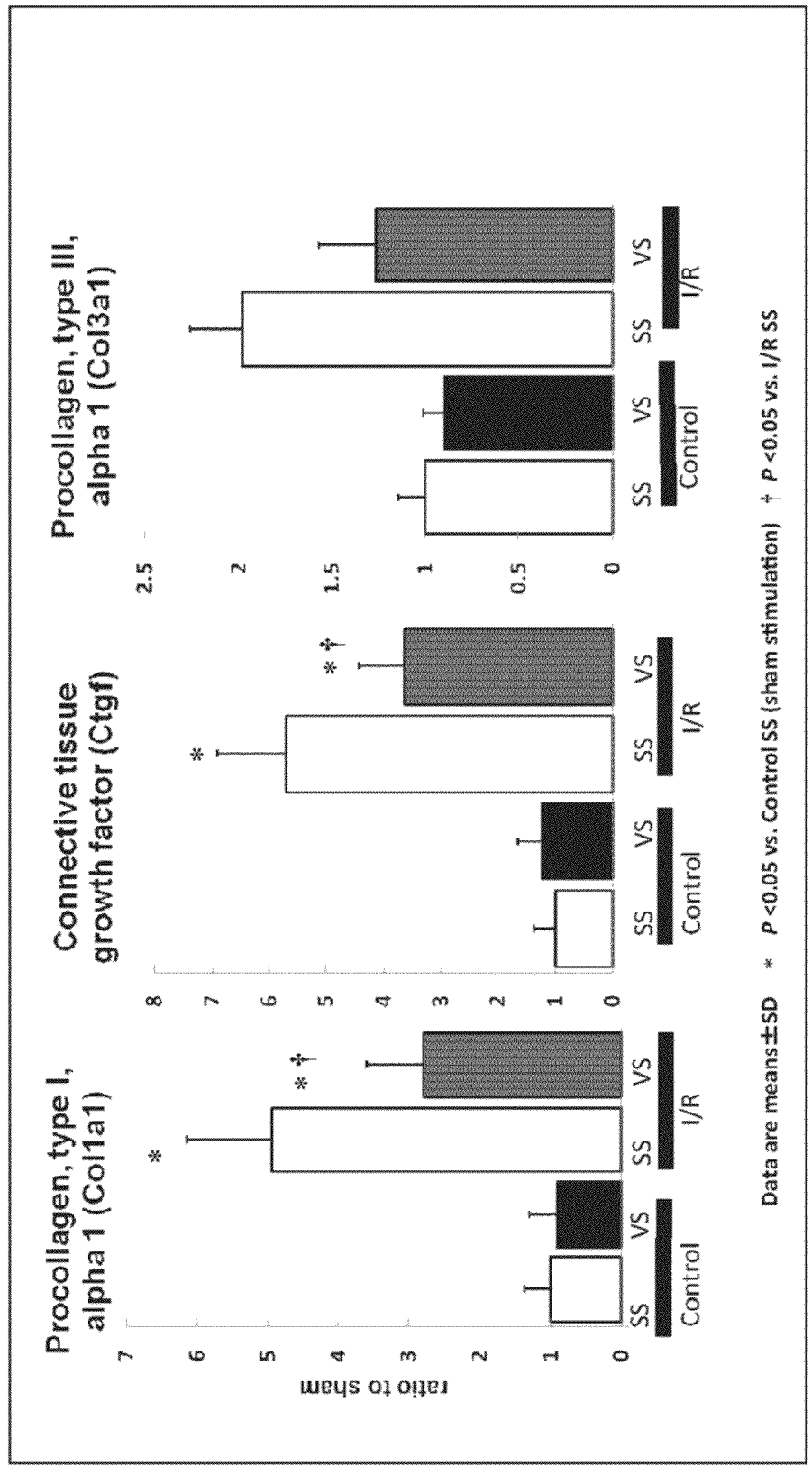
FIG. 6 is a drawing illustrating the expression of mRNA related to the production of collagen in the infarction site (measured using the real time PCR method).

Furthermore, the appearance of apoptosis at the myocardial infarction site was studied as the mechanism of the anti-modeling effect due to vagus nerve stimulation (FIG. 5). Multiple TUNEL positive cells appear in the infarct area 24 hours after due to ischaemia reperfusion, however, it was found that these TUNEL positive cell were significantly suppressed in the myocardial infarction area after vagus nerve stimulation Moreover, when mRNA was collected from the myocardial infarction 3 hours after the myocardial infarction, and the amount of gene expression related to the generation of collagen was measured, it was evident that gene expression recognized as procollagen, type 1, type 3, and the connective tissue growth factor were significantly suppressed by vagus nerve stimulation. The results are illustrated in FIG. 6.

It is well known that varying magnetic field in a conductor generates electric currents, generally referred to as Eddy currents. Therefore, effects similar to those arising from the electrical stimulation may be achieved by applying time-varying magnetic field, such as pulses. Based on such basic electromagnetic properties, devices to apply magnetic stimulation, which gets eventually converted to electrical stimulation based on induced Eddy currents in a biological subject, may be configured for treating certain types of diseases. Magnetic stimulation can be applied externally to the skin surface of a patient without surgically making an incision to reach the target site. Furthermore, applying magnetic pulses to the skin surface of a human or an animal body does not stimulate dermal nerves so that the pain level of the patient during the stimulation can be kept minimal. Thus, magnetic stimulation is preferable to electrical stimulation in medical treatments in view of the QOL stand point.

As mentioned earlier, it has been reported that transcranial magnetic stimulation is effective for treating depression. Additionally, similar magnetic stimulations are known to be effective for other types of disease including epilepsy, dystonia and Parkinson disease. Referring back to FIG. 9, an example of a device for applying magnetic stimulation is illustrated along with its electrical and magnetic characteristics. A magnetic stimulator manufactured by Magstim® is selected for illustrating this example. A photo in the upper left section of FIG. 9 shows a magnetic pulse application unit, including a coil in a package, connected to a magnetic pulse generation unit. The coil can be made of a conducting material such as copper, nickel or any other proper metal, and the packaging material can be a plastic, silicone or any other conventional insulating material. The drawing in the upper right section of FIG. 9 illustrates the coil winding and the magnetic field associated with the coil current. The 3D plot in the lower left section of FIG. 9 illustrates the magnetic field strength generated around the coil, exhibiting high strength around the center of the coil. The set of plots in the lower right section of FIG. 9 shows electrical and magnetic characteristics associated with an applied pulse. These plots illustrate a case in which a pulse of the coil current having a peak value of about 8000 Amps with a fast rise for about 0.1 msec and a slow falling tail for about 0.9 msec is applied; the corresponding magnetic pulse is generated, having a peak value of about 2.5 Tesla (in terms of magnetic flux density, B) with the same rise and fall characteristics for the time period of about 1 msec; and correspondingly the current in the tissues of a biological subject, such as a human or an animal, is induced, initially having a peak value of about 15 mA/cm$^2$ (in terms of current density) with a fast decrease and a slow recovery to zero for the time period of about 1 msec. Additionally, the plots of the rate of change of magnetic field, the induced electric field and the induced charge density, which are associated with the present pulse, are presented therein.

Referring back to FIG. 8, it is illustrated that a decrease in heart rate of a biological subject, which is a dog in this particular example, is observed when magnetic pulses are applied to the neck region of the dog. This experiment was conducted to confirm that application of time-varying magnetic field induces currents in the biological tissues, which in turn stimulates the vagus nerve, thereby decreasing the heart rate as in the case of the direct electrical stimulation. Specifically, the bottom plot illustrates the application of the magnetic stimulation in the form of a pulse train with 5 Hz for about 20 seconds, corresponding to applying 100 pulses continuously. The middle plot illustrates the observed decrease in blood pressure during the application period. The top plot illustrates that about 10% decrease in heart rate is observed with the application of the magnetic pulse train to the neck region.

Figure 8:
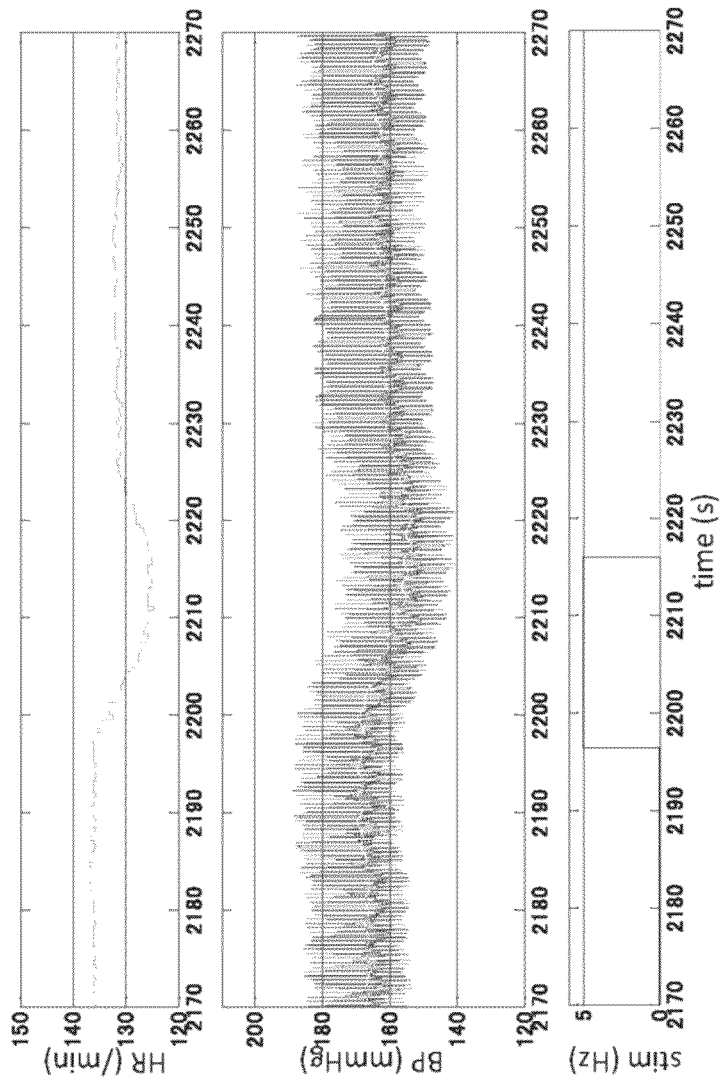
FIG. 8 is a drawing suggesting that, because the heart rate dropped when an existing magnetic stimulation device was applied to the neck region of a dog, the vagus nerve was stimulated by an electric field that was generated by generating a magnetic field.

Similar effects as illustrated in FIG. 8 can be observed when magnetic stimulation is applied to the chest region of a biological subject. Specifically, magnetic pulses are applied in the chest region in the proximity of the right atrium of the subject so as to stimulate the vagus nerve. Parameters associated with generation of the magnetic pulses can be controlled to obtain more than 5% decrease in heart rate, or more than 10% decrease in some cases.

Figure 10:
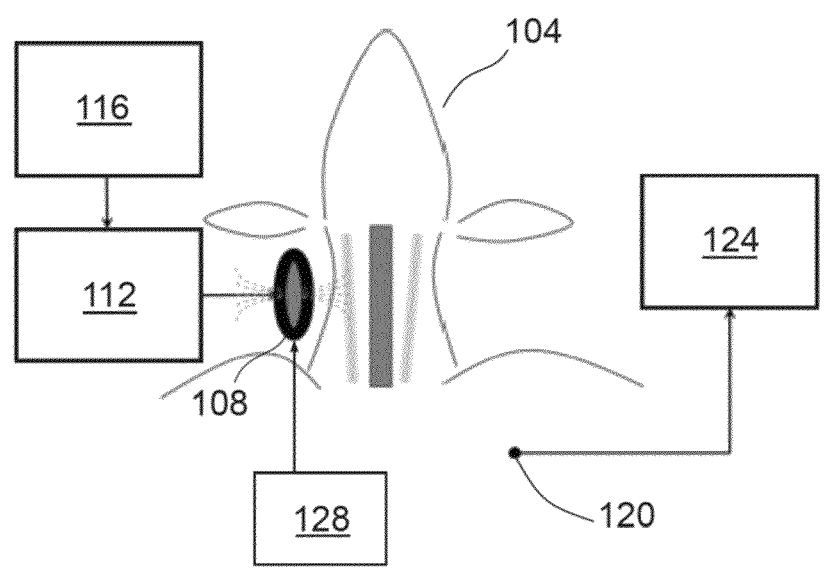
FIG. 10 illustrates an example of a configuration for applying magnetic stimulation to a biological subject for the purpose of treating cardiovascular disease.

FIG. 10 illustrates an example of a configuration for applying magnetic stimulation to a biological subject for the purpose of treating cardiovascular disease. The biological subject 104 may be a human or an animal, whose neck region is subject to the application of magnetic pulses. As explained earlier, the chest region may alternatively be subject to the application of magnetic pulses for the purpose of treating cardiovascular disease. The present magnetic stimulation device includes a magnetic pulse application unit 108, a magnetic pulse generation unit 112 and a control unit 116. The magnetic pulse application unit 108 includes a coil made of a conducting material such as copper, nickel or any other proper metal, the coil being packaged with a packaging material that can be a plastic, silicone or any other conventional insulating material. Copper is preferable for the present implementation, since its conductivity generally increases by cooling. The magnetic pulse application unit 108 is configured for placement on the skin surface of the neck region or chest region of a human or an animal. The magnetic pulse application unit 108 is coupled to the magnetic pulse generation unit 112. The control unit 116 is coupled to the magnetic pulse generation unit 112 and configured to control it for generation of magnetic pulses. The control unit 116 may be integrated with the magnetic pulse generation unit 112. Alternatively, the magnetic pulse generation unit may be configured to be controlled externally, manually or by any other control means to adjust parameters associated with the generation of magnetic pulses. Specifically, such adjustable parameters may include: the frequency and amplitude of the magnetic pulse, the time duration of continuous application of the pulses (i.e., length of a pulse train), and the inter-train interval (i.e., time duration when the pulses are not applied between the pulse trains). Vital signs of the biological subject can be detected by using conventional detectors. For example, the heart rate can be detected by use of a heart rate detection probe 120, which may be coupled to a heart rate monitor 124. One or more detectors or detection probes may be externally placed on the biological subject. Thus, all mechanical elements in this configuration can be placed externally to the body of the biological subject, without having to surgically incise or remove any part of the body.

A coil for generating magnetic pulses tends to heat up during operation due to rapidly changing coil currents, thereby necessitating provision of a cooling means. The present magnetic stimulation device may further include a cooling unit 128, which is coupled to the magnetic pulse application unit 108 and configured to generate cool air and circulate it along the coil winding. FIGS. 11A-11D illustrate an air flow pattern along the coil winding, which is configured to be double-layered in this example. FIG. 11A illustrates a top view of the double-layered coil winding 204-1 and 204-2 and the air flow 208-1 and 208-2 depicted with dashed lines. FIG. 11B illustrates a side view of the double-layered coil winding 204-1 and 204-2, where the air is flowing from the first layer down to the second layer as indicated by dashed line 208-3. FIG. 11C illustrates a top view of the first-layer coil winding 204-1 and the air flow 208-1 going inwardly toward the center along the first-layer coil winding 204-1. FIG. 11D illustrates a top view of the second-layer coil winding 204-2 and the air flow 208-2 going outwardly from the center along the second-layer coil winding 204-2. In this example, the coil winding is configured to be double-layered so that the air flow can be inputted to flow along the first-layer coil winding toward the center inwardly, flow down to the second layer at the center, and flow along the second-layer coil winding from the center outwardly. Thus, the overall area of the coil winding in contact with the cool air flow is maximized. Instead of a double-layer structure, the coil winding can be configured to be other structures as long as effective cooling is achieved by optimizing the area of the coil winding in contact with the cool air without sacrificing efficiency of the magnetic field generation based on the coil structure.

Parameter values associated with magnetic pulses may be adjusted by using the control unit 116 or any other control means, depending on effectiveness for treating the disease, variation in response among different patients, and other factors. The frequency of a magnetic pulse may range between 5 Hz and 30 Hz to avoid over and under stimulus. The pulse width may be in the range of 50 µsec-2 msec. The amplitude and time variation of a magnetic pulse may be adjusted so as to induce current density of about 15 mA/cm$^2$, as indicated in FIG. 9, in the tissues of a biological subject. Various experiments were carried out to optimize parameters associated with the magnetic pulses for achieving more than 5% decrease in heart rate, or more than 10% decrease in some cases, when the magnetic pulses are applied compared to the heart rate when the magnetic pulses are not applied. It was found that application of multiple pulse trains with a certain inter-train interval is effective in lowering heart rate of the patient as well as in avoiding the overheat of the coil. Here, a pulse train is defined as a series of continuous magnetic pulses; and an inter-train interval is defined as the time period between the pulse trains when the pulses are not applied. The length of a pulse train in the range between 6-20 seconds and the inter-train interval in the range between 40-54 seconds were found to be optimal. Application of a pulse train with a subsequent non-application period may be repeated for one treatment. That is, multiple pulse trains with a certain inter-train interval are applied for the treatment. The time duration of the application of multiple pulse trains with a certain inter-train interval in the range between 0.5-96 hours was found to be optimal. In addition to providing inter-train intervals, the cooling unit 128 may be operated for effective cooling. Instead of magnetic pulses having amplitudes in the positive direction, pulses in the form of burst may be used. In the burst application, the direction of the magnetic field swings between positive and negative directions, thereby giving rise to stronger effects.

Similar to the case of the electrical stimulation, the magnetic stimulation can be performed in conjunction with reperfusion therapy. Referring back to Embodiment 1, the similar experiments were carried out by applying the magnetic stimulation. Here, the magnetic pulse application unit is placed on the skin surface of the neck region of a biological subject. As explained earlier, the chest region may alternatively be stimulated. Results similar to those for the case of applying the electrical stimulation were obtained for the case of applying the magnetic stimulation as well, in that the effect is especially prominent when the magnetic stimulation is started before the reperfusion therapy for treating acute myocardial infarction.

Specifically, the upper right graph in FIG. 4, labeled LVESD, is one example illustrating the treatment effect under three different scenarios, where LVESD stands for Left Ventricular End-Systolic Dimension in mm, per TABLE 1. These three different scenarios are: Control, SS and VS, where Control represents a group for which only thoracotomy was performed; SS represents a group for which sham stimulation, i.e., mere placement of the magnetic pulse application unit on the neck region with no coil current, was performed; and VS represents a group for which the vagus nerve stimulation was performed by applying magnetic pulses to the skin surface of the neck region or chest region. The reperfusion therapy was performed after 30 minutes of ischemia for SS and VS, and the magnetic stimulation was performed for at least 30 minutes from the time of ischemia for VS. Thus, SS represents a group for which only the reperfusion therapy is performed, and VS represents a group for which the vagus nerve stimulation is started before the reperfusion therapy. As shown in the LVESD graph of FIG. 4, the vagus nerve stimulation that is started before the reperfusion (VS) suppresses an increase in the left ventricle size as compared to the case of performing only the reperfusion (SS). This procedure can be provided by configuring the magnetic pulse generation unit to generate the magnetic pulses to start the vagus nerve stimulation before the reperfusion therapy.

The graph in FIG. 5, labeled TUNEL Positive cells, is another example illustrating the treatment effect under three different scenarios, i.e., Control, SS and VS. As shown in this graph, the generation of apoptosis cells at the myocardial infarction site is reduced due to the vagus nerve stimulation (VS) compared to the case of performing only the reperfusion (SS).

It is to be understood that the above-described embodiments are illustrative of only a few of the many possible specific embodiments that can represent applications of the principles of the invention. Numerous and varied other arrangements can be readily devised by those skilled in the art without departing from the spirit and scope of the invention.

What is claimed is:

1. A method for treating cardiovascular disease in a human or an animal, the method comprising:
   placing a magnetic pulse application unit including a coil on a skin surface of a region of the human or the animal; and
   generating magnetic pulses around the coil, the magnetic pulses inducing currents in tissues in the region of the human or the animal to stimulate a vagus nerve,
   wherein the generating magnetic pulses to stimulate the vagus nerve is performed in conjunction with reperfusion therapy, wherein the cardiovascular disease is acute myocardial infarction.

2. The method of claim 1, wherein
the region is a neck region.

3. The method of claim 1, wherein
the region is a chest region.

4. The method of claim 1, further comprising:
cooling the coil by providing an air flow along a winding of the coil.

5. The method of claim 1, wherein
the generating magnetic pulses to stimulate the vagus nerve starts before the reperfusion therapy.

6. The method of claim 1, wherein
the generating magnetic pulses comprises generating magnetic pulses so as to obtain more than 5% decrease in heart rate of the human or the animal when the magnetic pulses are applied compared to the heart rate when the magnetic pulses are not applied.

7. The method of claim 1, wherein
the generating magnetic pulses comprises generating magnetic pulses with a frequency in a range between 5 Hz and 30 Hz.

8. The method of claim 1, wherein
the generating magnetic pulses comprises generating a plurality of pulse trains with an inter-train interval for a time duration in a range between 0.5 hours and 96 hours.

9. The method of claim 8, wherein
the generating magnetic pulses comprises generating the pulse train for a time duration in a range between 6 seconds and 20 seconds and the inter-train interval in a range between 40 seconds and 54 seconds.

10. The method of claim 1, wherein
the generating magnetic pulses comprises generating magnetic pulses having an amplitude and a time variation to induce the currents of about 15 mA/cm$^2$ in the tissues.

11. A magnetic stimulation device for treating cardiovascular disease in a human or an animal comprising:
   a magnetic pulse application unit including a coil configured for placement on a skin surface of a region of the human or the animal; and
   a magnetic pulse generation unit coupled to the magnetic pulse application unit and configured to generate magnetic pulses around the coil, the magnetic pulses inducing currents in tissues in the region of the human or the animal to stimulate a vagus nerve,
   wherein the cardiovascular disease is acute myocardial infarction, and the magnetic stimulation device is used in conjunction with reperfusion therapy.

12. The magnetic stimulation device of claim 11, wherein
the region is a neck region.

13. The magnetic stimulation device of claim 11, wherein
the region is a chest region.

14. The magnetic stimulation device of claim 11, further comprising:
   a cooling unit coupled to the magnetic pulse application unit and configured to provide an air flow along a winding of the coil to cool the coil.

15. The magnetic stimulation device of claim 11, wherein
the magnetic pulse generation unit is configured to be controlled to generate magnetic pulses to stimulate the vagus nerve before the reperfusion therapy.

16. The magnetic stimulation device of claim 11, further comprising:
   a control unit configured to control the magnetic pulse generation unit for generation of the magnetic pulses.

17. The magnetic stimulation device of claim 11, wherein
the magnetic pulse generation unit is configured to be controlled for generation of the magnetic pulses so as to obtain more than 5% decrease in heart rate of the human or the animal when the magnetic pulses are applied compared to the heart rate when the magnetic pulses are not applied.

18. The magnetic stimulation device of claim 11, wherein the magnetic pulse generation unit is configured to be controlled for generation of the magnetic pulses with a frequency in a range between 5 Hz and 30 Hz.

19. The magnetic stimulation device of claim 11, wherein the magnetic pulse generation unit is configured to be controlled to generate a plurality of pulse trains with an inter-train interval for a time duration in a range between 0.5 hours and 96 hours.

20. The magnetic stimulation device of claim 19, wherein the magnetic pulse generation unit is configured to be controlled to generate the pulse train for a time duration in a range between 6 seconds and 20 seconds and the inter-train interval in a range between 40 seconds and 54 seconds.

21. The magnetic stimulation device of claim 11, wherein the magnetic pulse generation unit is configured to be controlled to generate the magnetic pulses having an amplitude and a time variation to induce the currents of about 15 mA/cm$^2$ in the tissues.

\* \* \* \* \*